(12) United States Patent
Hotter

(10) Patent No.: US 9,670,188 B2
(45) Date of Patent: Jun. 6, 2017

(54) PROCESS FOR THE PREPARATION OF CRYSTALLINE FORM IV OF POSACONAZOLE

(71) Applicant: Sandoz AG, Basel (CH)

(72) Inventor: Andreas Hotter, Kundl (AT)

( * ) Notice: Subject to any disclaimer, the term of this patent is extended or adjusted under 35 U.S.C. 154(b) by 0 days.

(21) Appl. No.: 14/907,310

(22) PCT Filed: Jul. 24, 2014

(86) PCT No.: PCT/EP2014/065914
§ 371 (c)(1),
(2) Date: Jan. 25, 2016

(87) PCT Pub. No.: WO2015/011224
PCT Pub. Date: Jan. 29, 2015

(65) Prior Publication Data
US 2016/0168133 A1    Jun. 16, 2016

(30) Foreign Application Priority Data

Jul. 25, 2013 (EP) ..................................... 13178018

(51) Int. Cl.
*C07D 405/14* (2006.01)
*A61K 31/496* (2006.01)

(52) U.S. Cl.
CPC .......... *C07D 405/14* (2013.01); *A61K 31/496* (2013.01)

(58) Field of Classification Search
None
See application file for complete search history.

(56) References Cited

FOREIGN PATENT DOCUMENTS

| WO | 9517407 A1 | 6/1995 |
|---|---|---|
| WO | 9638443 A1 | 12/1996 |
| WO | 9918097 A1 | 4/1999 |
| WO | 2010000668 A1 | 1/2010 |
| WO | 2011144653 A1 | 11/2011 |
| WO | 2013042138 A2 | 3/2013 |

*Primary Examiner* — Emily Bernhardt
(74) *Attorney, Agent, or Firm* — Luedeka Neely Group, P.C.

(57) ABSTRACT

The present invention relates to an improved large scale process for the preparation of posaconazole form IV.

10 Claims, 1 Drawing Sheet

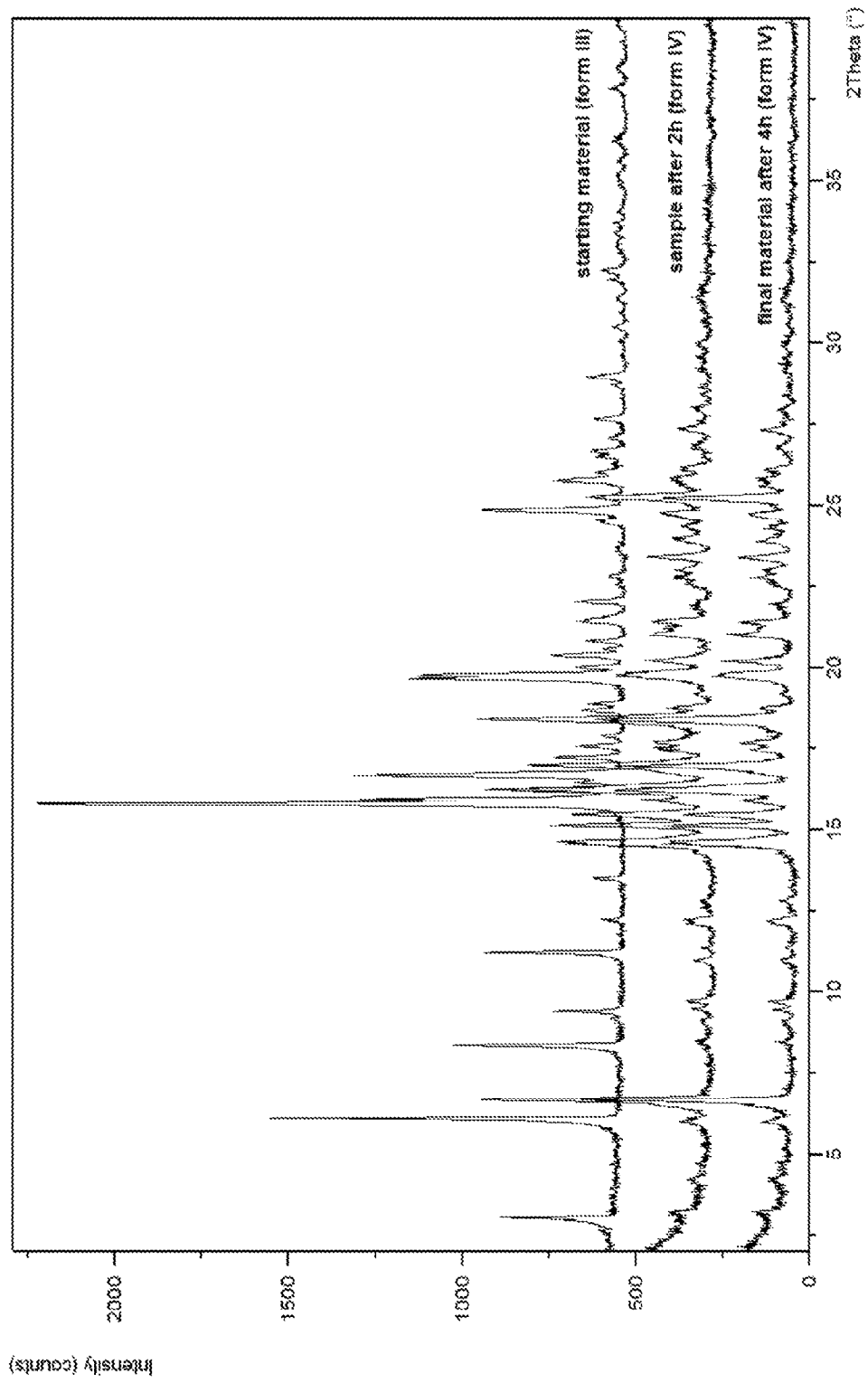

PROCESS FOR THE PREPARATION OF CRYSTALLINE FORM IV OF POSACONAZOLE

This application is a national phase entry of PCT International application number PCT/EP2014/065914, filed Jul. 24, 2014. This application also claims the benefit of the earlier filing date of EP 13178018.1, filed Jul. 25, 2013.

FIELD OF THE INVENTION

The present invention relates to an improved large scale process for the preparation of posaconazole form IV.

BACKGROUND OF THE INVENTION

Posaconazole (CAS registry number: 171228-49-2, CAS name: 2,5-anhydro-1,3,4-trideoxy-2-C-(2,4-difluorophenyl)-4-[[4-[4-[4-[1-[(1S,2S)-1-ethyl-2-hydroxypropyl]-1,5-dihydro-5-oxo-4H-1,2,4-triazol-4-yl]phenyl]-1-piperazinyl]phenoxy]methyl]-1-(1H-1,2,4-triazol-1-yl)-D-threo-pentitol) which is represented by the following chemical structure (I)

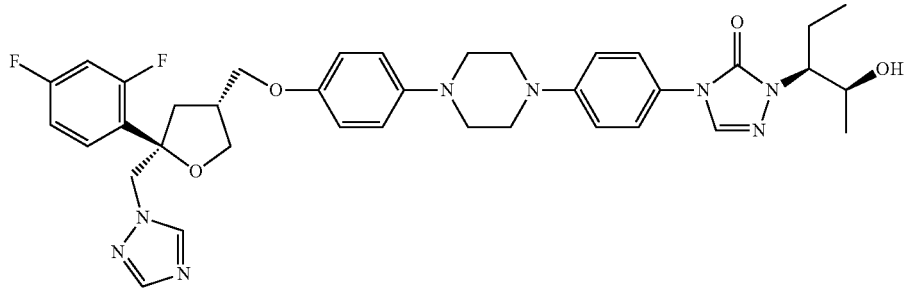

is a triazole antifungal agent available as an oral suspension (40 mg/mL) under the tradename Noxafil®.

WO 95/17407 A1 and WO 96/38443 A1 disclose the compound having the chemical structure (I) and its use in treating fungal infections.

WO 2010/000668 A1 discloses crystalline form IV of posaconazole and pharmaceutical compositions comprising the same. In addition methods of preparing crystalline form IV of posaconazole are disclosed.

WO 2011/144653 A1 (page 51, lines 17-27) discloses that posaconazole form IV is obtained by the solvent-mediated solid state transformation process according to WO 2010/000668 A1 and a concrete example for the preparation of form IV is given in example 6 of WO 2011/144653 A1.

However, the processes described in WO 2010/000668 A1 have the drawbacks of long and inconsistent solvent-mediated solid state transformation times. Hence, there is a need for an optimized process for the preparation of crystalline form IV of posaconazole with reduced and constant transformation times in order to increase the operational capacity and to reduce production costs on large scale.

SUMMARY OF THE INVENTION

The present invention refers to a large scale process for the preparation of posaconazole form IV comprising the steps of:
(a) providing a suspension or dispersion of:
  (i) posaconazole, wherein posaconazole is selected from crystalline form III of posaconazole and
  (ii) methanol and
(b) slurrying the suspension or dispersion at a temperature of 20-30° C.;
(c) adding water to the suspension or dispersion,
(d) adding posaconazole form IV seed crystals to the suspension or dispersion,
(e) slurrying the suspension or dispersion at 40-60° C. until the solvent-mediated solid state transformation to posaconazole form IV is complete,
(f) cooling the suspension or dispersion to a temperature of 20-30° C.,
(g) isolating form IV of posaconazole and
(h) drying form IV of posaconazole.

The processes for posaconazole form IV production disclosed in WO 2010/000668 A1 which are also used in example 6 of WO 2011/144653 A1 have the drawbacks of long and inconsistent solvent-mediated solid state transformation times.

In contrast the process of the present invention yields crystalline form IV of posaconazole in a fast and constant manner. Consequently, due to its increased operational capacity and reduced production costs, the process of the present invention is especially suitable for large scale production of posaconazole form IV.

Other objects, features, advantages and aspects of the present invention will become apparent to those of skill from the following description. It should be understood, however, that the description and the following specific examples, while indicating preferred embodiments of the invention, are given by way of illustration only. Various changes and modifications within the spirit and scope of the disclosed invention will become readily apparent to those skilled in the art from reading the description and from reading the other parts of the present disclosure.

BRIEF DESCRIPTION OF THE DRAWINGS

FIG. 1: Overlay of the X-ray powder diffractograms from example 1 of the present invention; top diffractogram: starting material (form III), middle diffractogram: solvent-mediated transformation after 2 hours (form IV), bottom diffractogram: solvent-mediated transformation after 4 hours respectively finally isolated material (form IV)

DETAILED DESCRIPTION OF THE INVENTION

The present invention refers to a large scale process for the preparation of posaconazol form IV comprising the steps of:

(a) providing a suspension or dispersion of:
  (i) posaconazole, wherein posaconazole is selected from crystalline form III of posaconazole and
  (ii) methanol and
(b) slurrying the suspension or dispersion at a temperature of 20-30° C.;
(c) adding water to the suspension or dispersion,
(d) adding posaconazole form IV seed crystals to the suspension or dispersion,
(e) slurrying the suspension or dispersion at 40-60° C. until the solvent-mediated solid state transformation to posaconazole form IV is complete,
(f) cooling the suspension or dispersion to a temperature of 20-30° C.,
(g) isolating form IV of posaconazole and
(h) drying form IV of posaconazole.

Posaconazole form III of WO 99/18097 A1 is applied as starting material in the process of the present invention. Form III can be produced by recrystallizing crude posaconazole from methanol e.g. according to the procedure provided in example 6 of WO 99/18097 A1. Crude posaconazole can be obtained e.g. according to the procedure disclosed in example 32 of WO 95/17407 A1.

In a first step a suspension/dispersion of posaconazole form III in methanol is prepared. The initial posaconazole concentration in methanol preferably ranges from about 25 to 75 g/L, more preferably from about 40 to 60 g/L, and most preferably the concentration used is about 50 g/L. The obtained suspension/dispersion is slurried in methanol at a temperature preferably ranging from about 20 to 40° C., more preferably from about 20 to 30° C. and most preferably at a temperature of about 25° C. for a time preferably ranging from about 30 to 240 minutes, more preferably from about 45 to 120 minutes and most preferably for about 60 minutes which leads to a homogenous suspension/dispersion lacking agglomerates.

Water is added only after slurrying posaconazole form III in methanol whereat the water/methanol ratio of the final suspension/dispersion is about 4:1 (v:v). The addition rate is not critical e.g. the water can be poured at once into the methanol suspension/dispersion or may be slowly added e.g. over a period of about 0.5 to 6 hours. The temperature of the applied water ranges from about 20 to 40° C., preferably from about 20 to 30° C., more preferably the temperature is about 25° C. and most preferably the water has approximately the same temperature as the before prepared methanol suspension/dispersion.

The posaconazole concentration in the water/methanol mixture preferably ranges from about 1 to 20 g/L, more preferably from about 5 to 15 g/L, and most preferably the concentration is about 10 g/L.

In a next step form IV seed crystals are added to the water/methanol suspension/dispersion. It is crucial to add the form IV seed crystals after the water addition as posaconazol form IV transforms to form III in the presence of pure methanol. The amount of seeds may range from about 1 to 10 w % related to the initially applied posaconazol form III amount.

The thus obtained suspension/dispersion is characterized by lacking agglomerated posaconazole particles which ensures a uniform dispersion of posaconazole within the slurry. This homogenous suspension/dispersion leads to an optimal solvent contact of the solid posaconazole material which is crucial for a fast and complete solvent-mediated solid state transformation.

The solvent-mediated solid state transformation is preferably performed at a temperature ranging from about 40 to 65° C., more preferably from about 55 to 65° C. and most preferably at a temperature of about 60° C. The suspension is stirred at the applied temperature until the solvent-mediated transformation to crystalline form IV of posaconazole is complete. Pure form IV is preferably obtained after stirring the suspension for about 1 to 6 hours, more preferably for about 1 to 4 hours and most preferably for about 1 to 2 hours. The completeness of the transformation can be confirmed by taking a sample and measuring an X-ray powder diffractogram of the dried sample.

After complete transformation the suspension is cooled to 25° C. and the crystals are isolated, whereat any conventional method such as filtration or centrifugation may be applied.

Finally the isolated posaconazole form IV may be dried under vacuum at a temperature preferably ranging from about 25 to 60° C., more preferably from about 25° C. to 55° C. and most preferably from about 25° C. to 45° C. Drying is preferably conducted for about 1 to 72 hours, more preferably for about 1 to 48 hours and most preferably for about 1 to 24 hours.

Inventive Step

In order to achieve a fast and reliable solvent-mediated solid state transformation from form III to form IV it is crucial that the solid posaconazole is well dispersed in the solvent system to ensure sufficient solvent contact. This can be achieved by the preparation of a homogenous suspension which lacks agglomerated particles as the inner core of agglomerates is not in contact with the solvent leading to a slow or even incomplete transformation.

According to the processes for form IV production disclosed in WO 2010/000668 A1 the posaconazole starting material is suspended in pure water (example 3 of WO 2010/000668 A1) or in a mixture of water and methanol (examples 1, 2 and 4 of WO 2010/000668 A1 and example 6 of WO 2011/144653). Such obtained posaconazole suspensions contain agglomerates leading to a decreased solvent contact of the solid posaconazole which consequently results in prolonged solvent-mediated solid state transformation times.

In addition it should be noticed that examples 1 to 4 of WO 2010/000668 A1 were performed on a 54 to 500 mg scale using magnetic stirring. Due to the grinding effect of magnetic stirrers agglomerates are usually destroyed, which influences the homogeneity of a suspension positively. Nevertheless the solvent-mediated solid state transformation was still very slow in examples 1-4 of WO 2010/000668 A1 as can be seen from table 1 of the present invention, which summarized the provided transformation times.

TABLE 1

Transformation times disclosed in examples 1-4 of WO 2010/000668 A1

| example | scale [mg] | transformation time |
| --- | --- | --- |
| 1 | 250 | 6 days |
| 2 | 500 | 3 days + overnight |
| 3 | 54 | 48 h |
| 4 | 250 | 3 h + overnight |

Especially on large scale, were usually no magnetic stirring is applied, the solvent-mediated solid state transformation from crystalline form III to form IV was found to be slow and inconsistent when following the procedure disclosed in WO 2010/000668 A1. E.g. pure form IV was obtained after 30 hours in the best case and only after almost 9 days in the worst case. (see reference examples 6a-6f of the present invention).

The inventors of the present invention surprisingly found that slurrying posaconazole form III in methanol prior to water and seed crystal addition leads to a homogenous suspension/dispersion lacking agglomerates, which consequently decreases the solvent mediated transformation time to pure form IV dramatically. E.g. when form III of posaconazole was slurried in methanol prior to water and seed crystal addition for some time the solvent-mediated solid state transformation to form IV was complete within 4 hours (see examples 1-4 of the present invention). Hence slurrying posaconazole form III in methanol prior to water and seed crystal addition is the key step for obtaining form IV in a fast and reliable manner especially on large scale.

The present invention therefore provides an optimized process for the preparation of form IV with significantly reduced and constant solvent-mediated solid state transformation times. Due to its increased operational capacity and the reduced production costs the process of the present invention is especially suitable for large scale production of form IV.

EXAMPLES

X-ray powder diffractograms were obtained with a PANalytical X'Pert PRO diffractometer equipped with a theta/theta coupled goniometer in transmission geometry, Cu-K$\alpha$1,2 radiation (wavelength 0.15419 nm) with a focusing mirror and a solid state PIXcel detector. The diffractograms were recorded at a tube voltage of 45 kV and a tube current of 40 mA, applying a stepsize of 0.013° 2-Theta with 40 seconds per step (255 channels) in the angular range of 2° to 40° 2-Theta at ambient conditions. A typical precision of the 2-Theta values is in the range of about ±0.2° 2-Theta. Thus a diffraction peak that appears at 5.0° 2-Theta can appear between 4.8 and 5.2° 2-Theta on most X-ray diffractometers under standard conditions.

Preparation of Crystalline Form IV of Posaconazole—Best Mode

Example 1

A mixture of 30.1 g crude posaconazole (e.g. prepared according to example 32 of WO 95/17407 A1) and 600 mL methanol was heated to reflux, whereat a clear solution was obtained. The solution was cooled to 35° C. within one hour and further cooled to 25° C. within an additional hour, whereat crystallization occurred. The obtained suspension was slurried at 25° C. for 1 hour whereat a homogenous suspension lacking agglomerates was obtained.

Thereafter 2400 mL water were added under stirring before 0.3 g posaconazole form IV seeds (e.g. obtained according to the procedure disclosed in example 1 of WO 2010/000668 A1) were added to the suspension. The mixture was heated to a jacket temperature of 60° C. ($T_{mass}$=56-59° C.) and stirred at the same. An XRPD sample taken after 2 hours confirmed the receipt of pure form IV. The suspension was stirred for additional 2 hours before it was cooled to 25° C. Thereafter the material was isolated by filtration and pre-dried on the filter by suction. The wet product was then further dried under vacuum 40 mbar) at 45° C. overnight to obtain 28.7 (94% yield) of posaconazole form IV.

Complete transformation to form IV of posaconazole was confirmed by XRPD. The corresponding diffractograms from the starting material (form III), the sample taken after 2 hours (form IV) and the finally isolated material after 4 hours of slurrying (form IV) are displayed in FIG. 1 of the present invention.

Example 2

A mixture of 30.1 g crude posaconazole (e.g. prepared according to example 32 of WO 95/17407 A1) and 600 mL methanol was heated to reflux, whereat a clear solution was obtained. The solution was cooled to 35° C. within one hour and further cooled to 25° C. within an additional hour, whereat crystallization occurred. The obtained suspension was then cooled to −5° C. before the material was isolated by filtration. The wet filter cake was transferred back into the reactor and 600 mL methanol were added. The suspension was slurried at 25° C. for 1 hour resulting in a homogenous suspension lacking agglomerates before 2400 mL water were added under stirring. Thereafter 0.3 g posaconazole form IV seeds (e.g. obtained according to the procedure disclosed in example 1 of WO 2010/000668 A1) were added to the suspension. The mixture was heated to a jacket temperature of 60° C. ($T_{mass}$=56-59° C.) and stirred at the same. An XRPD sample taken after 2 hours confirmed the receipt of pure form IV. The suspension was further stirred for 2 hours before it was cooled to 25° C. Thereafter the material was isolated by filtration and pre-dried on the filter by suction. The wet product was then further dried under vacuum 40 mbar) at 45° C. overnight to obtain 26.0 g (86% yield) of posaconazole form IV.

Example 3

A mixture of 30.1 g crude posaconazole (e.g. prepared according to example 32 of WO 95/17407 A1) and 600 mL methanol was heated to reflux, whereat a clear solution was obtained. The solution was then cooled to 35° C. within one hour and further cooled to 25° C. within an additional hour, whereat crystallization occurred. The obtained suspension was cooled to −5° C. before the material was isolated by filtration. The wet filter cake was transferred back into the reactor and 600 mL methanol were added. The suspension was slurried at 25° C. for 1 hour resulting in a homogenous suspension lacking agglomerates before 2400 mL water were added under stirring. Thereafter 2.1 g posaconazole form IV seeds (e.g. obtained according to the procedure disclosed in example 1 of WO 2010/000668 A1) were added to the suspension. The mixture was heated to a mass temperature of 43° C. and stirred at the same. An XRPD sample taken after 2 hours showed that only traces of form III were present. The suspension was further stirred for 2 hours before it was cooled to 25° C. The material was isolated by filtration and pre-dried on the filter by suction. The wet product was then further dried under vacuum 40 mbar) at 40° C. overnight to obtain 27.9 g (87% yield) of posaconazole form IV.

Example 4

A mixture of 30.1 g posaconazole form III (e.g. prepared according to example 6 of WO 99/18097 A1) and 600 mL methanol was slurried at 25° C. for 1 hour resulting in a homogenous suspension lacking agglomerates. Thereafter 2400 mL water were added under stirring before 0.3 g posaconazole form IV seeds (e.g. obtained according to the procedure disclosed in example 1 of WO 2010/000668 A1) were added to the suspension. The mixture was heated to a jacket temperature of 60° C. ($T_{mass}$=56-59° C.) and stirred at the same. An XRPD sample taken after 2 hours confirmed the receipt of pure form IV. The suspension was further stirred for 2 hours before it was cooled to 25° C. Thereafter the material was isolated by filtration and pre-dried on the filter by suction. The wet product was then further dried under vacuum 40 mbar) at 45° C. overnight to obtain 29.1 g (98% yield) of posaconazole form IV.

Table 2 summarizes the transformation times of examples 1-4 which have been performed according to the process of the present invention.

TABLE 2

Transformation times of examples 1-4 performed according to the procedure disclosed in the present invention

| example | scale [g] | transformation time |
|---|---|---|
| 1 | 30.1 | <4 h |
| 2 | 30.1 | <4 h |
| 3 | 30.1 | <4 h |
| 4 | 30.1 | <4 h |

As can be seen from table 2 the process of the present invention constantly yields form IV of posaconazole within 4 hours.

Small Scale Preparation of Crystalline Form IV of Posaconazole According to the Procedure Disclosed in WO 2010/000668 A1

Reference Example 5a

To 2.0 g posaconazole form III (e.g. prepared according to example 6 of WO 99/18097) and 0.2 g posaconazole form IV seeds (e.g. obtained according to the procedure disclosed in example 1 of WO 2010/000668 A1) 80 mL water and 20 mL methanol were added and the obtained suspension was stirred at 45° C. XRPD samples were taken after 2, 4 and 6 hours. After 24 hours the suspension was cooled to 25° C. and the material was isolated and dried at 45° C. under vacuum. The results are summarized in table 3 of the present invention.

Reference Example 5b

To 2.0 g posaconazole form III (e.g. prepared according to example 6 of WO 99/18097) and 0.2 g posaconazole form IV seeds (e.g. obtained according to the procedure disclosed in example 1 of WO 2010/000668 A1) 160 mL water and 40 mL methanol were added and the obtained suspension was stirred at 45° C. XRPD samples were taken after 2, 4 and 6 hours. After 24 hours the suspension was cooled to 25° C. and the material was isolated and dried at 45° C. under vacuum. The results are summarized in table 3 of the present invention.

TABLE 3

Transformation times of reference examples 5a-5b performed according to the procedure disclosed in WO 2010/000668 A1 on small scale

| examples | 2 h | 4 h | 6 h | 24 h |
|---|---|---|---|---|
| 5a | IV + III | IV + III | IV + III | III + IV |
| 5b | IV + III | IV + III | IV + III | IV + III |

As can be seen from table 3 following the procedure disclosed in WO 2010/000668 A1 the solid state transformation to pure form IV was still not complete after 24 hours.

Large Scale Preparation of Crystalline Form IV of Posaconazole According to the Procedure Disclosed in WO 2010/000668 A1

Reference Example 6a

A mixture of 80 L methanol and 4.0 kg crude posaconazole (e.g. prepared according to example 32 of WO 95/17407 A1) was heated to reflux, whereat a clear solution was obtained. The solution was cooled to 35° C. within 2 hours and further cooled to 15° C. within 2.5 hours, whereat crystallization occurred. The obtained suspension was further cooled to −5° C. and kept at the same temperature for 2 hours before the material was isolated by centrifugation. The wet filter cake was transferred back into the reactor and 330 g posaconazol form IV seeds (e.g. obtained according to the procedure disclosed in example 1 of WO 2010/000668 A1) were added. Thereafter 80 L water and 19.2 L methanol were added and the suspension was heated to a mass temperature of 43±2° C. and stirred at the same. Samples were taken every 4 hours in order to check the completeness of the transformation to form IV. After complete transformation the suspension was cooled to 25° C. and the material was isolated by centrifugation. The wet product was then dried under vacuum 30 mbar) at 40° C. for 15 hours to obtain 3.3 kg (76% yield) of posaconazole form IV. The transformation time of reference example 6a is summarized in table 4.

Reference Examples 6b-6f

Starting from different amounts of crude posaconazole (e.g. prepared according to example 32 of WO 95/17407 A1) the reference examples 6b-6f have been performed analogously to reference example 6a. The transformation times of reference examples 6b-6f are summarized in table 4.

TABLE 4

Transformation times of reference examples 6a-6f performed according to the procedure disclosed in WO 2010/000668 A1 on large scale

| example | scale [kg] | transformation time |
|---|---|---|
| 6a | 4.0 | 1 d 20 h |
| 6b | 6.2 | 1 d 11 h |
| 6c | 7.5 | 1 d 06 h |
| 6d | 6.8 | 1 d 16 h |
| 6e | 8.0 | 6 d 03 h |
| 6f | 6.0 | 8 d 22 h |

As can be seen from table 4 the solvent-mediated transformation to pure form IV of posaconazole was slow and inconsistent when following the procedure of WO 2010/000668 A1. Especially in two cases the transformation was extremely slow (reference example 6e and 6f).

The invention claimed is:
1. A process for the preparation of crystalline form IV of posaconazole comprising the steps of:
  (a) providing a suspension or dispersion of:
    (i) posaconazole, wherein posaconazole is selected from crystalline form III of posaconazole and
    (ii) methanol and

(b) slurrying the suspension or dispersion at a temperature of 20-30° C. for a time ranging from about 30 to 240 minutes prior to addition of any water or seed crystals;

(c) thereafter, adding water to the suspension or dispersion, (d) adding posaconazole form IV seed crystals to the suspension or dispersion, (e) slurrying the suspension or dispersion at 40-60° C. until the solvent-mediated solid state transformation to posaconazole form IV is complete, (f) cooling the suspension or dispersion to a temperature of 20-30° C., (g) isolating form IV of posaconazole and (h) drying form IV of posaconazole.

2. A process according to claim 1, wherein the posaconazole concentration in the initial methanol suspension is 50 g/L.

3. A process according to claim 1, wherein the methanol water ratio during the solvent-mediated solid state transformation from posaconazole form III to posaconazole form IV is 4:1 (v:v).

4. A process according to claim 1, wherein the posaconazole concentration during the solvent-mediated solid state transformation in methanol/water is 10 g/L.

5. A process according to claim 1, wherein the posaconazole form IV seed crystals are added after the water addition.

6. A process according to claim 1, wherein the amount of seed crystals applied ranges from 1 to 10 w % related to the initially applied amount of posaconazole form III starting material.

7. A process according to claim 1, wherein the temperature during the solvent-mediated solid state transformation ranges from 40 to 49° C.

8. A process according to claim 1, wherein the temperature during the solvent-mediated solid state transformation ranges from 50 to 60° C.

9. A process according to claim 1, wherein the solvent-mediated solid state transformation is complete within 4 hours.

10. A process according to claim 1, wherein the solvent-mediated solid state transformation is complete within 2 hours.

* * * * *